United States Patent [19]

Ihrman et al.

[11] Patent Number: 5,103,059
[45] Date of Patent: Apr. 7, 1992

[54] PROCESS FOR ALKYLATION OF AROMATIC DIAMINES

[75] Inventors: Kryn G. Ihrman, Baton Rouge, La.; Olan W. Mitchell, Glen Carbon, Ill.; R. Woodrow Wilson, Jr., Baton Rouge, La.

[73] Assignee: Ethyl Corporation, Richmond, Va.

[21] Appl. No.: 601,516

[22] Filed: Oct. 23, 1990

[51] Int. Cl.$^5$ .................... C07C 209/60; C07C 209/00
[52] U.S. Cl. ..................... 564/409; 564/305; 502/155
[58] Field of Search ............. 564/409, 408, 305; 502/155

[56] References Cited

U.S. PATENT DOCUMENTS 3,275,690  9/1966  Stroh et al. ............. 564/409
4,128,582  12/1978  Governale et al. ......... 260/578

FOREIGN PATENT DOCUMENTS 0350681  1/1990  European Pat. Off. ......... 564/409
2426395  12/1974  Fed. Rep. of Germany ...... 564/409

OTHER PUBLICATIONS

Stroh, et al., *Newer Methods of Preparative Organic Chemistry*, vol. 2, "Alkylation of Aromatic Amines", Wilhiho Foerst, Editor, Academic Press (1963).

*Primary Examiner*—Glennon H. Hollrah
*Assistant Examiner*—Shailendra Kumar
*Attorney, Agent, or Firm*—Richard J. Hammond

[57] ABSTRACT

Production of alkyl substituted aromatic diamines by reacting triethylaluminum with an aromatic diamine and a chloride ion source in the presence of an olefin is disclosed. The alkyl substituted aromatic diamines are useful as chain extenders in polyurethane processes.

14 Claims, No Drawings

PROCESS FOR ALKYLATION OF AROMATIC DIAMINES

FIELD OF THE INVENTION

This invention relates to a process for producing aromatic diamines and is more particularly concerned with a novel catalyst for said process.

BACKGROUND OF THE INVENTION

Aromatic amines having unsubstituted hydrogen atoms in positions ortho to amino groups may be alkylated in the ortho position in a number of ways.

Kolka, et al, U.S. Pat. No. 2,814,646, describes alkylation of aromatic amines having unsubstituted ortho positions by reacting the aromatic amine with an aliphatic olefin in the presence of an aluminum trianilide catalyst. The aromatic amine may have additional substituents provided that there is an unsubstituted position ortho to an amino group available for alkylation.

The catalyst of Kolka, et al, is prepared in a process which reacts the aromatic amine, having at least one hydrogen bonded to the amino nitrogen, with aluminum metal, aluminum alkyl, aluminum amide, and the like. Between about 0.1-20% of the aromatic amine is converted to the aluminum anilide type catalyst. The Kolka, et al, process may be conducted between the temperatures of about 250° C. up to decomposition temperature, e.g., 400° C., under olefin pressure.

Stroh, et al, U.S. Pat. No. 3,275,690, is an improvement over the Kolka, et al, process by including a small amount of Friedel-Crafts catalyst as a promoter. Stroh, et al, mentions aluminum chloride, aluminum bromide, iron chloride, boron trifluoride, zinc chloride, stannic chloride, and the like as examples of promoters. The amount of promoter used is disclosed to be between 0.05 and 10 wt. % of the amount of aromatic amine utilized. The alkylation temperature is between about 150° C. and about 400° C. under olefin pressure.

Klopfer, U.S. Pat. No. 3,923,892, provides a similar method of ortho alkylation of aromatic amines utilizing an alkyl aluminum halide catalyst, such as diethylaluminum chloride or ethylaluminum sesquichloride. The amount of catalyst required provides about one gram atom of aluminum per each 5-40 gram moles of aromatic amine. A portion of the aluminum may be provided by reacting aluminum metal with the aromatic amine.

Governale, et al, U.S. Pat. No. 4,128,582, describes a process of selective ortho-alkylation of aromatic amines using an aluminum anilide catalyst in which the reaction rate is increased by addition of a hydrogen halide to the alkylation mixture. The process is conducted by reacting an aromatic amine with an olefin in the presence of the aluminum anilide catalyst at a temperature of between about 200-500° C. A hydrogen halide may be added to the reaction mixture as a promoter in an amount to provide up to two halogen atoms per aluminum atom.

THE INVENTION

According to the present invention, there is provided an improved process for alkylation of aromatic diamines. The process of this invention comprises reacting triethylaluminum with an aromatic diamine and a chloride ion source in the presence of an olefin. For the purposes of this application, the term chloride ion source shall refer to sources which will provide chloride ions in the reaction medium. The ratios listed involving chloride ion sources shall refer to sources which will provide chloride ions in the molar ratio indicated.

In the process of alkylation, the best results are obtained when the aromatic diamine has two primary amino groups and a replaceable hydrogen on the ring in an ortho position relative to such amino groups.

One embodiment of this invention involves a catalyst of triethyl aluminum (TEA) and a chloride ion source in a ratio of TEA to chloride ion source of between about 0.9:0.01 and about 10:0.9, preferably in a ratio of about 1.0:0.5.

In the above embodiment of the present invention, the process is conducted at an elevated temperature. The process is usually carried out at a temperature between about 250° C. and about 350° C. Preferably, the process of the present invention is carried out at an elevated temperature in the range of between about 280° C. and about 320° C., most preferably at between about 290° C. and about 310° C.

A further preferred embodiment of the present invention involves conducting the process under an elevated pressure. While the reaction may be conducted at lower pressures (i.e., above atmospheric pressure), the reaction rate, and therefore yield, are generally not sufficiently high at lower pressure. In contrast, the use of relatively high pressures does not inhibit the process, but tend to be confined by equipment limitations. The pressure falls in a range of between about 700 psi and about 5000 psi. Preferably, the process is conducted at a pressure of between about 900 psi and about 1100 psi. Most preferably, the process is conducted at a pressure of between about 950 psi and 1050 psi.

In the process of this invention, various aromatic diamines may be used providing that each aromatic diamine contains two replaceable hydrogens on the ring, each in an ortho position relative to an amino group. These aromatic diamines include those having the structure:

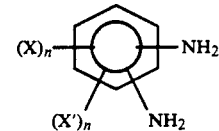

wherein X and X' are alkyl groups of 1 to 6 linear or branched chain carbon atoms and n is an integer that is 0 or 1. X and X' are the same or different and further are exemplified by the group of methyl, ethyl, propyl, butyl, pentyl, hexyl, isopropyl, isobutyl, isopentyl, isohexyl, sec-butyl, neopentyl, tert-pentyl, 1-methylpentyl, 2-methylpentyl, 3-methylpentyl, 1-methylbutyl, 2-methylbutyl, 1,2-methylbutyl, 2,3-methylbutyl, 1-ethylbutyl, 1-ethylpropyl, phenyl, phenoxy, hexyloxy, pentyloxy, butoxy, propoxy, ethoxy, methoxy, allyloxy, isopropoxy, isobutoxy, sec-butoxy, tert-butoxy, and the like.

Of the above described aromatic diamines, the toluene diamines (i.e., 2,4-toluenediamine, 2,5-toluenediamine, 2,6-toluenediamine, 3,5-toluenediamine, and 3,4-toluenediamine) are preferred.

The chloride ion sources useful in the process include compounds that will not produce a counter ion which will inhibit the reaction (i.e., alkali metal chlorides).

Examples of useful sources are hydrogen chloride, aluminum chloride, ethylaluminum chloride, diethylaluminum chloride and ethylaluminum sesquichloride. In addition, compounds that will decompose to give hydrogen chloride or ionize to give a chloride ion, such as acyl halides, benzyl chloride and allyl chloride, may be utilized.

The olefins useful in the process include olefins which are both mono- or poly-unsaturated, cyclic or acyclic, substituted or unsubstituted, and both terminal and internal olefins. Examples of acyclic monoolefins are ethylene, propylene, butene-1, butene-2, isobutene, pentene-1, isopentene, pentene-2, hexene-1, hexene-2, 2-methyl pentene-1, 2-methyl pentene-2, n-decene-1, 2-ethyl octene-1, 2-ethyl octene-2, n-decene-2, dodecene-1, 2-ethyl decene-1, 2-ethyl decene-2, and the like.

Examples of cyclic monoolefins are cyclopentene, cyclohexene, cyclooctene, 1-methylcyclohexene, 1-butylcyclohexene, 1-methylcyclooctene, and the like.

Useful acyclic polyenes include 1,3-butadiene, 2-methyl-1,3-butadiene, 2,3-dimethyl-1,3-butadiene, 1,4-pentadiene, and the like. Some useful cyclic polyenes are cyclopentadiene, dicyclopentadiene, 1,3-cyclooctadiene, 1,3-cyclopentadiene, 1,4-octadiene, 1,3,5-cyclooctatriene, and the like.

The substituted olefins can have any substituents that do not interfere with the reaction. Examples of such groups are halogens, alkoxy groups, aryloxy groups, aryl radicals, and the like. Illustrative examples of such olefins are 2-chloro-1,3-butadiene, vinyl chloride, vinyl bromide, indene, α-methyl styrene, 4-dodecyl styrene, 4-sec-octyl-α-methyl styrene, and the like.

The preferred olefin reactants are acyclic monoolefins containing from 1–6 carbon atoms, cyclic olefins containing 5 to 8 carbon atoms and aryl-substituted monoolefins containing from 8 to 12 carbon atoms. Especially preferred are the lower hydrocarbon monoolefins containing from 1–6 carbon atoms such as ethylene, propylene, butene-1, isobutene, pentene-1, pentene-2, isopentene, hexene-1, hexene-2, 2-methyl pentene-1, cyclohexene, and the like.

The amount of olefin added to the aromatic diamine will vary depending upon whether mono- or dialkylation is desired. The precise amount is not a critical feature of the process as long as sufficient olefin is present to provide at least a monoalkylated product. Generally, from about 2 mole equivalents to about 20 mole equivalents of olefin are added for each mole of aromatic amine. A more preferred range is from about 3 mole equivalents to 5 mole equivalents of olefin for each mole equivalent of aromatic amine.

The amount of catalyst used in the process should be sufficient to catalyze the alkylation at a reasonable rate. The amount of catalyst can be expressed in terms of moles of aromatic diamine per mole of aluminum in the catalyst. Satisfactory results are generally obtained when about 3 to 18 moles of aromatic diamine are used per mole of aluminum in the catalyst system. A more preferred range is from about 7 to 13 moles of aromatic diamine per mole of aluminum in the catalyst system.

The process should be conducted under a substantially inert atmosphere. Excessive amounts of oxygen or moisture will destroy the catalyst and halt the alkylation. The reactants, however, do not have to be completely anhydrous, but should be substantially anhydrous. Also, the amount of oxygen and moisture can be minimized. This is generally accomplished by flushing the reaction vessel with an inert gas such as nitrogen, neon, methane, ethane or propane prior to conducting the reaction. For the purposes of this application, "inert" shall refer to any substance that is resistant to chemical or physical action under the conditions of the present invention.

The reaction can be conducted in the presence of an inert solvent. Suitable solvents include aliphatic and aromatic hydrocarbons. Examples of aliphatic hydrocarbons that may be used include decane, undecane, dodecane, tridecane, tetradecane, pentadecane and hexadecane, among others. Useful aromatic hydrocarbons include toluene, xylene, mesitylene, and the like.

The catalyst system is readily prepared from commercial stock of each component. The components may be mixed and the mixture is either used immediately or stored for later use. In addition, the catalyst components may be added to the reaction vessel either as a mixture or separately. It is the stoichiometric relationship of the catalyst to the reactants that is controlling.

The time required for alkylation depends upon the reaction conditions, such as reaction temperature, pressure, amount of catalyst and ratio of catalyst components, as well as the particular aromatic diamine and olefin used. Alkylation generally requires from 1 to 4 hours, with a preferred reaction time being from 1.5 to 3 hours.

The alkylation catalyst is prepared by reacting the aromatic diamine with an alkylaluminum chloride or with a mixture of aluminum alkyl and a chloride ion source. After mixing the reagents, the reaction mixture is heated to about 150 C. to insure complete reaction. The mixture is then charged to an autoclave and heated to the reaction temperature. The olefin is introduced to the autoclave starting at about 200° C. and the pressure is adjusted to the desired reaction pressure at the reaction temperature. Additional olefin is added during the course of the reaction to maintain the desired pressure.

After the alkylation reaction is completed, the reaction vessel is cooled and the excess olefin is vented off. An excess of 25% sodium hydroxide is then added to hydrolyze the aluminum salts. The resulting aqueous phase consisting of water, sodium hydroxide and sodium aluminate is separated from the organic phase. The organic phase is then transferred for distillation.

The present invention provides an improved process for alkylation of aromatic diamines and reducing the amount of heavy end formation. The term "heavy end formation" refers to products formed by various condensations or polymerizations such as the formation of dimer, trimer, tetramer, etc., such reactions producing compounds with molecular weight in excess of about 220.

The following examples are provided as illustrations of the present invention but are not intended to limit the present invention to the conditions illustrated.

It should be noted that a relatively low chloride ion concentration in the reaction vessel substantially increases the rate of reaction. However, larger concentrations tend to reduce the reaction rate and therefore reduce yield.

EXAMPLE I 170.8 grams of premelted toluene diamine (about 80% 2,4-toluene diamine and 20% 2,6-toluene diamine) were added into a 500 ml 4-neck flask equipped with a stirrer, condenser, thermometer and dropping funnel. To this was added, dropwise, 13.0 g of diethylaluminum chloride. The temperature was raised to about 150° C.

and held for 15 minutes. This mixture was transferred to an autoclave and held at 1000 psig $N_2$. The $N_2$ was vented and heating begun up to about 300° C. as ethylene was added to bring the pressure up to about 1000 psig. These conditions were maintained for about 4 hours with samples taken at half hour intervals. The samples were subjected to area % gas chromatography to determine the reaction mixture compositions of toluene diamine (TDA), monethyl TDA, and 2,4- and 2,6-diethyl toluene diamine (DETDA). Kugelrohr distillation was utilized to determine amounts of heavy end formation. The percent compositions of each sample were as follows:

| Sample | Time of Reaction (Hours) | Diamine (TDA) | Monoethyl TDA | 2,4-DETDA | 2,6-DETDA |
|---|---|---|---|---|---|
| 1 | ½ | 42.30 | 41.42 | 8.05 | 1.89 |
| 2 | 1 | 33.34 | 45.09 | 11.84 | 2.76 |
| 3 | 1½ | 29.91 | 45.06 | 13.16 | 3.11 |
| 4 | 2 | 28.22 | 45.01 | 13.84 | 3.28 |
| 5 | 2½ | 26.14 | 45.17 | 14.84 | 3.52 |
| 6 | 3 | 24.73 | 44.96 | 15.37 | 3.68 |
| 7 | 3½ | 23.83 | 45.19 | 15.97 | 3.81 |
| 8 | 4 | 23.77 | 44.93 | 15.93 | 3.81 |

A Kugelrohr distillation was conducted at about 140° C. and less than 1 mm of mercury on a 92.32 g sample of the final DETDA mixture from Example I. The distillation revealed heavy end formation of approximately 13.63% of the DETDA mixture by weight.

EXAMPLE II

Into a 500 ml 4-neck flask equipped with a stirrer, condenser, thermometer and dropping funnel was added 170.8 g of toluene diamine (approximately 80% 2,4-toluene diamine and 20% 2,6-toluene diamine). To this was added 12.4 g of triethylaluminum, dropwise. This mixture was raised to a temperature of about 150° C. for about 15 minutes and then transferred to an autoclave and held at 1000 psig $N_2$. The $N_2$ was vented and temperature raised to about 300° C. as ethylene was added to bring the pressure up to about 1000 psig. These conditions were maintained for about four hours with samples removed hourly to determine reaction mixture composition by area percentage gas chromatography. The percent composition of toluene diamine (TDA), monoethyl TDA and 2,4- and 2,6-diethyl toluene diamine (DETDA) were determined. The percent compositions of each sample were as follows:

| Sample | Time of Reaction (Hours) | Diamine (TDA) | Monoethyl TDA | 2,4-DETDA | 2,6-DETDA |
|---|---|---|---|---|---|
| 1 | 1 | 4.40 | 29.52 | 49.68 | 14.17 |
| 2 | 2 | 0.38 | 4.00 | 73.76 | 19.17 |
| 3 | 3 | 0.23 | 2.65 | 74.55 | 19.07 |
| 4 | 4 | 0.14 | 1.92 | 74.43 | 18.77 |

A Kugelrohr distillation of a 99.70 g sample of the final DETDA mixture of Example II conducted at about 140° C. and less than 1 mm of mercury indicated heavy end formation amounting to 3.73% of DETDA compounds by weight.

EXAMPLE III

Into a 500 ml 4-neck flask equipped with a stirrer, condenser, thermometer and dropping funnel was added 170.8 g of toluene diamine (approximately 80% 2,4-toluene diamine and 20% 2,6-toluene diamine). To this was added a mixture of 9.3 g triethylaluminum (TEA and 3.25 g diethylaluminum chloride (DEAC). The TEA/DEAC mixture was added dropwise to control the rate of gas formation. The mixture was then transferred to an autoclave and held overnight at 1000 psig $N_2$. The $N_2$ was vented and temperature raised to about 300° C. as ethylene was added to bring the pressure up to about 1000 psig. These conditions were maintained for about three hours with samples removed at half-hour intervals to determine reaction mixture composition by area percentage gas chromatography. The percent compositions of toluene diamine (TDA), monoethyl TDA and 2,4- and 2,6-diethyl toluene diamine (DETDA) for each sample were as follows:

| Sample | Time of Reaction (Hours) | Diamine (TDA) | Monoethyl TDA | 2,4-DETDA | 2,6-DETDA |
|---|---|---|---|---|---|
| 1 | ½ | 18.72 | 48.66 | 24.24 | 6.04 |
| 2 | 1 | 2.36 | 19.59 | 59.60 | 15.54 |
| 3 | 1½ | 0.27 | 1.73 | 75.41 | 19.08 |
| 4 | 2 | 0.17 | 0.95 | 75.62 | 19.04 |
| 5 | 2½ | 0.15 | 0.84 | 75.37 | 18.94 |
| 4 | 3 | 0.13 | 0.77 | 75.11 | 18.80 |

A Kugelrohr distillation was conducted at about 140° C. and less than 1 mm of mercury on a 99.83 g sample of the final DETDA mixture from Example III. The distillation revealed heavy end formation amounting to 4.98% of the DETDA mixture by weight.

EXAMPLE IV

Into a 500 ml 4-neck flask equipped with a stirrer, condenser, thermometer and dropping funnel was added 170.8 g of premelted TDA (same composition as Examples I-III). To this was added dropwise a mixture of 6.17 triethylaluminum and 6.51 g diethylaluminum chloride. The mixture was then transferred to an autoclave and pressurized to 1000 psig under nitrogen. The nitrogen was vented and the temperature raised to about 300° C. as ethylene was added to bring the pressure up to about 1000 psig. These conditions were maintained for about two hours with samples taken at half-hour intervals to determine reaction mixture composition by area percentage gas chromatography. The percent composition of toluene diamine (TDA), monoethyltoluene diamine (METDA) and 2,4- and 2,6-diethyl toluene diamine (DETDA) for each sample were as follows:

| Sample | Time of Reaction (Hours) | Diamine (TDA) | Monoethyl TDA | 2,4-DETDA | 2,6-DETDA |
|---|---|---|---|---|---|
| 1 | ½ | 9.30 | 42.50 | 36.39 | 9.11 |
| 2 | 1 | 0.35 | 3.10 | 74.08 | 19.10 |
| 3 | 1½ | 0.19 | 1.01 | 75.25 | 19.15 |
| 4 | 2 | 0.11 | 0.74 | 74.81 | 18.98 |

A Kugelrohr distillation was conducted at about 140° C. and less than 1 mm of mercury on a 100.02 g sample of the final DETDA mixture of Example IV. The distillation revealed heavy end formation of approximately 3.64% of the DETDA mixture by weight.

What is claimed is:

1. A process for alkylating aromatic diamines and inhibiting heavy end formation which comprises treating a mixture of an aromatic diamine and an olefin with a catalyst comprising triethylaluminum and a chloride ion source wherein the molar ratio of triethylaluminum to chloride ion source is from about 0.9:0.01 to about 1.0:0.5.

2. The process of claim 1 wherein said process is conducted under pressure in the range of above 700 psi to about 5000 psi.

3. The process of claim 2 wherein the process is conducted under pressure in the range of about 900 psi to about 1100 psi.

4. The process of claim 1 wherein the process is conducted at a temperature in the range of about 250° C. to about 350° C.

5. The process of claim 4 wherein the process is conducted at a temperature in the range of about 280° C. to about 320° C.

6. The process of claim 1 wherein said aromatic diamine is a $C_1$–$C_6$ linear or branched alkyl substituted diamine of the formula:

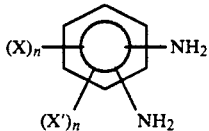

wherein X and X' are the same or different alkyl groups of 1 to 6 linear or branched chain carbon atoms, n is an integer that is 0 and the aromatic ring contains two replaceable hydrogen atoms, each in an ortho position relative to an amino group.

7. The process of claim 1 wherein said alkyl group is methyl or ethyl.

8. The process of claim 1 wherein said olefin is propylene, isobutylene or ethylene.

9. The process of claim 1 wherein the reaction is conducted without the presence of a solvent.

10. A process for alkylating a toluene diamine and inhibiting heavy end formation which comprises treating a mixture of a toluene diamine and an olefin with a catalyst formed by reacting triethylaluminum with a toluene diamine in the presence of a chloride ion source.

11. The process of claim 10 wherein said olefin is ethylene.

12. The process of claim 10 wherein the process is conducted under a pressure in the range of about 900 psi to about 1100 psi.

13. The process of claim 10 wherein the process is conducted at a temperature in the range of about 280° C. to about 320° C.

14. The process of claim 10 wherein the ratio of triethylaluminum to chloride ion source in the catalyst is 1.0:0.5.

* * * * *